United States Patent
Pfeiffer et al.

(10) Patent No.: US 7,329,595 B2
(45) Date of Patent: Feb. 12, 2008

(54) DEPOSITION OF CARBON-CONTAINING LAYERS USING VITREOUS CARBON SOURCE

(75) Inventors: Loren Neil Pfeiffer, Harding Township, Morris County, NJ (US); Kenneth William West, Mendham Township, Morris County, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 11/114,828

(22) Filed: Apr. 26, 2005

(65) Prior Publication Data

US 2006/0236936 A1  Oct. 26, 2006

(51) Int. Cl.
  *C23C 14/26* (2006.01)
(52) U.S. Cl. .......... 438/596; 438/565; 427/249.1; 118/726; 392/386; 392/387; 250/251
(58) Field of Classification Search ........ 118/726; 392/386, 387; 250/251, 492.1, 492.2; 427/249.1; 204/298.41; 438/565, 569
See application file for complete search history.

(56) References Cited

U.S. PATENT DOCUMENTS

| | | | |
|---|---|---|---|
| 4,239,955 A | | 12/1980 | Cho .................. 219/271 |
| 5,363,400 A | * | 11/1994 | Damond et al. .......... 373/10 |
| 5,405,659 A | * | 4/1995 | Fernandez ............ 427/596 |
| 5,622,567 A | * | 4/1997 | Kojima et al. .......... 118/726 |
| 5,897,790 A | * | 4/1999 | Koga et al. ............ 216/11 |

FOREIGN PATENT DOCUMENTS

| | | | |
|---|---|---|---|
| EP | 549207 | * | 6/1993 |
| JP | 59-33737 | * | 2/1984 |
| JP | 5933737 | | 2/1984 |
| JP | 61-86410 | * | 5/1986 |
| JP | 6186410 | | 5/1986 |
| JP | 08-236447 | * | 9/1996 |

OTHER PUBLICATIONS

R. J. Malik et al., "Carbon doping in molecular beam epitaxy . . . ," *Appl. Phys. Lett.*, vol. 53, No. 26, pp. 2661-2663 (Dec. 1988).
R. J. Malik et al., "Properties and applications of carbon-doped GaAs . . . ," *J. Crystal. Growth*, vol. 127, pp. 686-689 (1993).
M. Micovic et al., "Quantum well lasers with carbon doped cladding . . . ," *Appl. Phys. Lett.*, vol. 64, No. 4, pp. 411-413 (Jan. 1994).
A. Mak et al., Carbon filament source . . . , *J. Vac. Sci. Technol B.*, vol. 12, No. 3, pp. 1407-1409 (May/Jun. 1994).
EPI MBE Products Group, "High Performance Components To Make the Most of Your MBE System: 2000 Product Guide," p. 67.
MBE Komponenten, "Products 2003," pp. 38-39.

\* cited by examiner

*Primary Examiner*—Richard Bueker

(57) ABSTRACT

An effusion source comprises a vitreous C filament and a heater to increase the temperature of the filament to produce a C vapor. Also described is a deposition method comprising (a) depositing a layer of material on a substrate, and (b) during step (a), heating a body of material that includes vitreous carbon so that carbon from the body is vaporized and incorporated into the deposited layer.

13 Claims, 2 Drawing Sheets

DEPOSITION OF CARBON-CONTAINING LAYERS USING VITREOUS CARBON SOURCE

BACKGROUND OF THE INVENTION

1. Field of the Invention

This invention relates to the deposition of carbon-containing layers and, more particularly, to effusion cells and methods for their use in the molecular beam epitaxial (MBE) growth of such layers.

2. Discussion of the Related Art

Molecular beam deposition of layers of material (e.g., semiconductors, metals, insulators, or superconductors) on a heated substrate in an ultra high vacuum is well known in the art. In particular, MBE is one of the principal techniques used in the semiconductor device industry to fabricate high quality, single crystal, semiconductor layers with thickness control on the order of a monolayer. In MBE a single crystal substrate or wafer is placed in a vacuum chamber where it is heated. Effusion cells loaded with source materials in solid or liquid form are heated to vaporize the material and generate beams of constituent atoms, which are directed at the substrate. Alternatively, one or more of the effusion cells may be replaced by a gas jet coupled to a source of gaseous material to generate one or more of the requisite beams. (The latter deposition technique is known as chemical beam epitaxy, or CBE, especially if a chemical reaction occurs on the substrate surface during, or just before, incorporation of a component of the beam.) In both MBE and CBE the constituent atoms adsorb on the substrate surface and incorporate into the underlying crystal structure to form a layer. Control is so good that the layer is literally formed one monolayer at a time.

Although the term molecular is used to describe the vaporized source material in this deposition process, those skilled in the art understand that the source material may be elemental (or atomic) as well as compound (or molecular).

In the MBE growth of Group III-V compound semiconductor layers, for example, the crucible of one effusion cell would contain a Group III metal (e.g., liquid Ga), and the crucible of another cell would contain a Group V material (e.g., a solid source such as elemental As, or less commonly polycrystalline GaAs). On the other hand, in the CBE growth of such layers, one or more of the crucibles containing, for example, Group V material would be replaced by a gas source of, for example, arsine or phosphine. In either case, a third effusion cell or gas source would contain the source of a dopant. One consideration in the choice of a dopant is the conductivity-type of the layer to be grown. For example, to dope Group III-V compound layers n-type from a solid source tin (Sn) and silicon (Si) have been commonly used as dopants, and to dope such layers p-type from a solid source beryllium (Be) has been commonly used for many years. More recently, however, Be has been largely replaced by carbon (C).

Carbon has several characteristics that make it preferable as a p-type dopant in Group III-V compound layers deposited by MBE. First, Be is toxic; C is not. Second, Be has a relatively high vapor pressure and, therefore, during the high temperatures used in an MBE deposition processes, Be contaminates the growth chamber. Third, Be diffuses in the growing layer at a much higher rate than C. Therefore, precise control of the location and concentration of Be within very thin layers is difficult.

$CBr_4$ is currently used in the industry to provide a source of C. See, for example, page 67 of the Product Guide 2000 of the EPI MBE Product Group, St. Paul, Minn., which is incorporated herein by reference. However, Br is corrosive, and extreme care must be exercised in evacuating it from the deposition chamber. Alternatives to $CBr_4$ have been suggested in the prior art. For example, direct resistive heating of C filaments has been reported by R. J. Malik et al., *J. Cryst. Growth*, Vol. 127, pp. 686-689 (1993), which is incorporated herein by reference. Various methods for producing the C filaments have been tried including machining the filaments from a block of solid graphitic C or patterning them from a sheet of graphite foil. A. Mak et al., *J Vac. Sci. Technol. B*, Vol. 12, No. 3, pp. 1407-1409 (1994), which is also incorporated herein by reference, describe a woven filament that comprised a bundle of 6000, 10-µm-diameter graphite fibers. The fibers were clamped at both ends to a refractory metal support attached to an ultrahigh vacuum feed-through, as shown in FIG. 1 of the A. Mak et al. paper. The authors report a relatively short period of operation: only 15 hr at a power dissipation level corresponding to a hole concentration of $5 \times 10^{18}$ cm$^{-3}$ at 1 µm/hr growth rate. They also predict that repeated temperature cycling will shorten the filament lifetime.

We have found that, due to the relatively low resistivity of graphite filaments, they must be driven at relatively high input current levels to attain suitable doping levels. In addition, the high thermal conductivity of graphite filaments requires relatively high input power to attain requisite filament temperature. However, these high current and power levels tend to cause outgassing of the apparatus supporting the filament and of other components in the deposition system, which leads to undesirable contamination and, in turn, to decreased mobility of semiconductor layers grown in such systems.

On the other hand, a paper by R. J. Malik et al [*Appl. Phys. Lett.*, Vol. 53, No. 26, pp. 2661-2663 (1988)] and the product literature of MBE Komponenten GmbH, Germany [MBE Komponenten, Dr. Karl Eberl, Products 2003, pp. 38-39] both describe a C sublimation source that utilizes a pyrolytic graphite, serpentine filament. Both of these references are incorporated herein by reference. However, pyrolytic graphite also has relatively high electrical and thermal conductivity, which means that correspondingly high power/current must be applied to generate suitable doping levels. In addition, the typical serpentine shape of the filament employed in these references suffers from hot spots at the sharp bends, which tends to decrease the filament lifetime.

As pointed out in the Komponenten literature, these issues of C doping also apply to the deposition of other than Group III-V compound layers; e.g., the deposition of Si—C and Si—Ge—C alloys.

Thus, a need remains in the MBE deposition art for a source of C doping that operates at lower power/current levels, and hence produces less contamination, and has a relatively longer lifetime than is currently available from graphite filaments.

BRIEF SUMMARY OF THE INVENTION

In accordance with one aspect of our invention, an effusion source comprises a vitreous C filament and a heater to raise the temperature of the filament sufficiently to produce a C vapor. By vitreous C we mean that the C atoms are arranged in a tetrahedral structure akin to that found in amorphous diamond; i.e., each C atom is located at the center of an equilateral tetrahedron and is bonded in four directions pointing at the four vertices of the tetrahedron.

In a currently preferred embodiment, the heater provides electric current to the filament. In this regard, we have found that the resistivity of vitreous C is considerably higher than that of graphite, and its thermal conductivity is considerably lower, which means that correspondingly less input power/ current has to be applied to vitreous C filaments to achieve the same doping level. Accordingly, our vitreous C filaments produce considerably less contamination than graphite filaments.

In accordance with another aspect of our invention, a method comprises (a) depositing a layer of carbon-containing material on a substrate, and (b) during step (a), heating a body of material that includes vitreous carbon so that carbon from the body is vaporized and incorporated into the deposited layer.

By the phrase carbon-containing we mean that C is incorporated either as a dopant (e.g., C-doped GaAs) or as a primary constituent (e.g., a Si—C alloy).

BRIEF DESCRIPTION OF THE SEVERAL VIEWS OF THE DRAWING

Our invention, together with its various features and advantages, can be readily understood from the following more detailed description taken in conjunction with the accompanying drawing, in which.

DETAILED DESCRIPTION OF THE INVENTION

General Molecular Beam Deposition Apparatus

Figure 1:
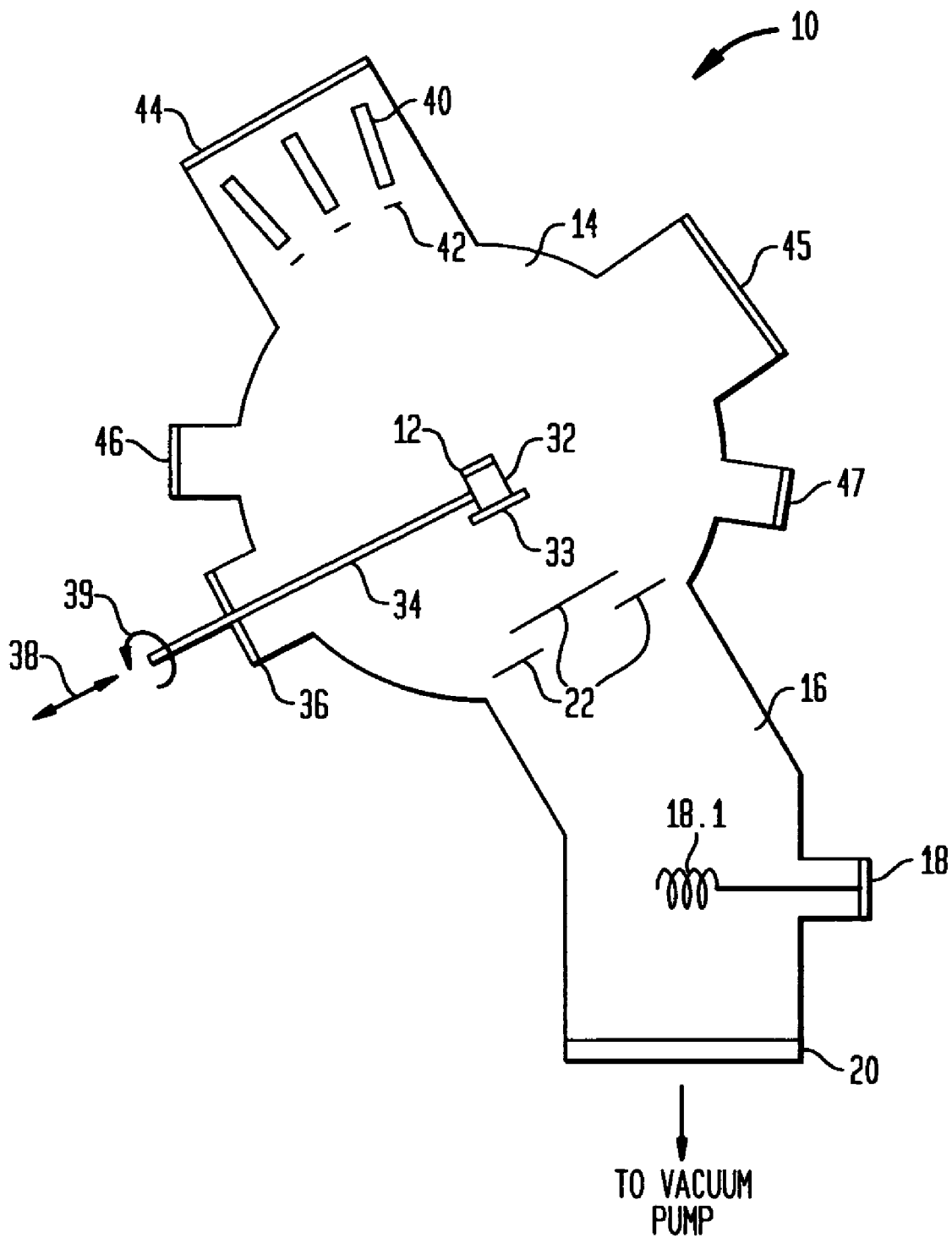
FIG. 1 is a schematic view of a prior art MBE apparatus.

Before discussing our invention in detail, we first turn to FIG. 1, which shows a well known ultra-high vacuum apparatus 10 for the molecular beam deposition of layers of, for example, semiconductor materials sequentially on a substrate 12. The apparatus 10, which is typically made of stainless steel, comprises a growth chamber 14 and a pump chamber 16. The growth chamber 14 is provided with a multiplicity of ports, which serve a variety of functions. For example, manipulator port 36 is used to position the substrate 12, oven port 44 is used to generate molecular beams, and viewing port 45 is used to visually observe the substrate. Additional ports 46 or 47 may be used to couple ion gauges (not shown) to the growth chamber. Illustratively, one ion gauge is used to monitor the chamber pressure; another is used to measure atomic or molecular beam flux.

Vacuum conditions (e.g., a base pressure of $10^{-9}$ to $10^{-12}$ Torr) are achieved and maintained in the growth chamber 14 by suitable pumping means, typically a Ti sublimation pump 18 coupled to a commercially available cryogenic vacuum pump (not shown) via port 20. The sublimation pump 18 includes a Ti element 18.1 positioned within a cryogenically cooled (e.g., liquid nitrogen) first shroud (not shown). A multiplicity of staggered, liquid-nitrogen-cooled baffles 22 blocks line-of-sight paths between element 18.1 and substrate 12.

The substrate 12 is mounted on a holder 32 and is heated by means of a suitable heater 33. Holder 32 is in turn secured to a manipulator illustrated as a rod 34 that extends through port 36 to the exterior of the apparatus. Arrows 38 and 39 indicate that the rod, and hence the substrate, may be translated or rotated, or both, into a desired position within the growth chamber. Typically the substrate is surrounded by a cryogenically cooled second shroud (not shown), which is apertured to allow access to the substrate surface by growth and test beams and for visual inspection.

As shown in FIG. 1, the manipulator has been used to locate the substrate 12 in a growth position. In this position substrate 12 faces a multiplicity of shuttered effusion cells 40, which are located in oven port 44 and are each surrounded by cryogenically cooled third shrouds (not shown). Cells 40 are loaded with source materials typically in a liquid or solid state, although in some cases the source materials may be gaseous. (In a liquid state, the source material is commonly referred to as a melt.) When suitably heated and the shutters 42 are opened, the solid or liquid source materials evaporate to form a multiplicity of beams of constituent materials (known as molecular beams) that are adsorbed onto the heated substrate 12 where they form, for example, a semiconductor layer. At least one of the cells 40 is a source of a dopant beam, and in particular, a filament source of generating a beam of C that is incorporated into the deposited layer, either as a dopant (e.g., in the case of p-type doping of Group III-V compounds) or as a primary constituent (e.g., in the case of Si alloys such as Si—C or Si—Ge—C).

Carbon may be incorporated into a device as a dopant in either (or both) of two well-known ways: by a bulk-doping process or by a delta-doping process. In bulk-doping, deposition of device layers continues while the C beam is on, so that C is incorporated into the layer as it is being deposited. In delta-doping, deposition of a layer is interrupted while the C beam remains on, so that C is deposited as a fraction of a monolayer (typically $10^{-3}$ of a monolayer) on the previously deposited layer.

Thus, when we state that our invention is used to deposit at least one layer of a carbon-containing material, in the context of doping we mean this phrase to include at least one bulk-doped layer that includes C as a dopant or at least one delta-doped layer (or fraction of a monolayer) of C itself. Of course, in the context of depositing C-containing layers in general, the phrase also includes depositing at least one bulk layer that includes C as a primary constituent.

Depending on the growth conditions and the nature of the substrate 12, the deposited semiconductor layer may be monocrystalline (single crystal), polycrystalline or amorphous. Although our invention is primarily concerned with high quality, monocrystalline, semiconductor layers, our effusion cells may also be used to fabricate semiconductor layers that are not monocrystalline or to fabricate non-semiconductor materials such as metals, insulators or superconductors.

Although modern designs of MBE apparatus have evolved considerably in the last 25 years, many of the features of a basic MBE apparatus are described by A. Y. Cho in U.S. Pat. No. 4,239,955 issued on Dec. 16, 1980, which is incorporated herein by reference.

CBE apparatus is essentially identical to the MBE apparatus described above, except that one or more of the effusion cells 40 is replaced by a gas source.

Other Vacuum Deposition Systems

Our C source, which is described below, may be useful in other types of vacuum deposition systems or apparatus as long as the mean free path of the carbon atoms/molecules is long enough that a sufficient number of them reach the substrate and are incorporated into the carbon-containing layer deposited thereon. In this regard, the system should provide a working vacuum of at least $10^{-3}$ Torr, and illustratively a base vacuum of $10^{-9}$ to $10^{-12}$ Torr, as mentioned above for MBE.

Carbon Filament Design

Figure 2:
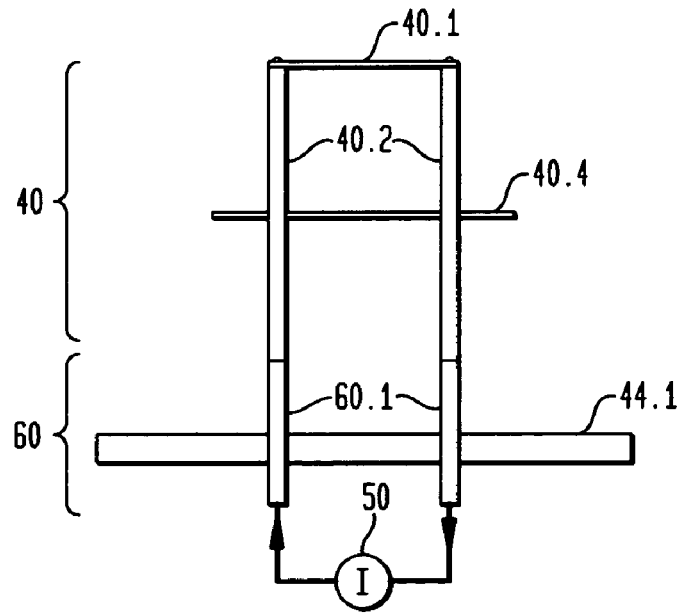
FIG. 2 is a schematic, cross sectional view of a fixture for a C filament, in accordance with one embodiment of our invention.

In accordance with one aspect of our invention, an effusion cell 40, as shown in FIG. 2, comprises a fixture for supporting a vitreous C filament 40.1 within the oven port 44 of, for example, a typical MBE apparatus of the type shown in FIG. 1. The fixture includes a pair of refractory metal rods 40.2 with filament 40.1 mounted on the coplanar ends of the rods 40.2. The refractory rods 40.2 are mechanically and electrically coupled to conductive metal rods 60.1 of a standard high vacuum feed-through 60 via a standard threaded bolt and bore arrangement (not shown). Feed-through 60 extends through a sidewall of the growth chamber 14 of FIG. 1, typically through a sidewall 44.1 of the oven port 44, to a power source 50 (e.g., a current source).

Mechanical stability is illustratively provided to the refractory rods 40.2 by means of an electrically insulating refractory holder 40.4.

Typically the refractory rods 40.1 comprise tantalum (Ta) or molybdenum (Mo) or alloys of either, the conductive rods 60.1 comprise copper (Cu), and the holder 40.4 comprises quartz.

Figure 3:
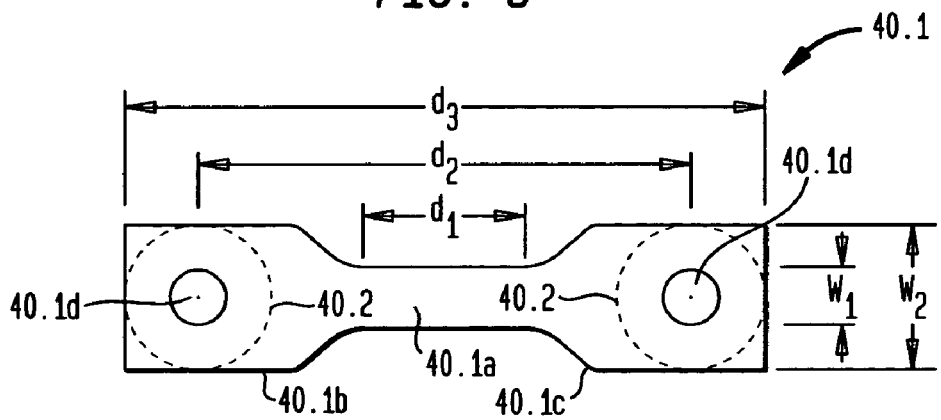
FIG. 3 is a schematic top view of the C filament of FIG. 1, in accordance with one embodiment of our invention.
Figure 4:
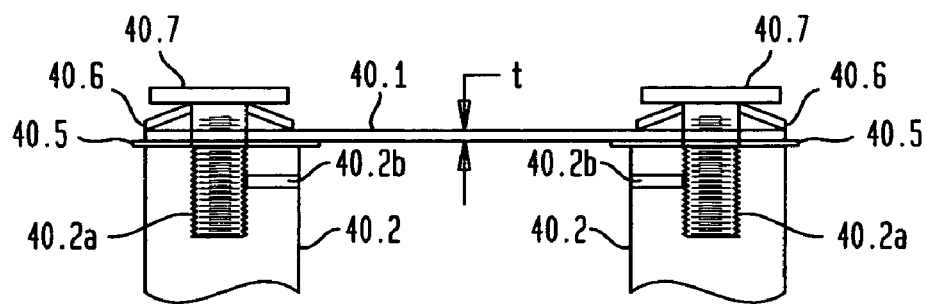
FIG. 4 is a schematic side view of the fixture of FIG. 1, in accordance with one embodiment of our invention.

In a preferred embodiment of our invention, as shown in FIG. 3, the vitreous C filament 40.1 is a thin, planar member that, in top view, has the general shape of a bar bell; that is, it includes a relatively narrow central portion or neck 40.1a disposed between and integrally connected to relatively wider end portions 40.1b. The latter portions have holes 40.1d aligned with corresponding threaded holes or bores 40.2a in the refractory rods 40.2, as shown in FIG. 4. Refractory metal bolts 40.7 extend through the holes 40.1d into the bores 40.2a in order to hold the filament 40.1 in place.

The neck 40.1a serves to concentrate electric current, and thus heat, in the narrower central portion of the filament 40.1 away from bolts 40.7, thereby decreasing the temperature of the bolts, which in turn decreases outgassing from the refractory rods 40.2, decreases the power required for a particular C flux, and also decreases the likelihood that they will react with other materials in the fixture. However, care should be exercised that the neck 40.1a does not become so hot that the vitreous C undergoes a phase transition to graphitic C. This phase transition has an onset at ~2300° C. and becomes more rapid as the temperature is raised further.

In addition, the filament 40.1 is secured in place by a spring-loaded arrangement, which illustratively includes a spring-loaded refractory metal washer 40.6 disposed between the head of each bolt 40.7 and the top surface of the filament. Illustratively, the washers 40.6 have a conical shape; e.g., they are well-known Belleville washers. Illustratively, the washers 40.6 comprise a material that retains its resiliency at temperatures above about 1400° C. Suitable materials include Ta alloys such as 1-10% W and 99-90% Ta. The bolts 40.7 typically comprise Ta, but may also comprise the same type of alloys used for the washers 40.6.

Refractory spacers 40.5 are disposed between the tops of the refractory rods 40.2 and the underside of the vitreous C filament 40.1. The spacer material should have a low vapor pressure and should have little or no reaction with either the refractory rods 40.2 or the vitreous C filament 40.1 at the operating temperature of the effusion cell 40. Preferably the spacers 40.5 comprise rhenium (Re) foil, but tungsten (W) foil or alloys of either could also be used.

Finally, the refractory rods 40.2 are each provided with a hole 40.2b, which extends radially from the exterior surface of the rod to the bore 40.2a, thereby enabling the bores 40.2a to be pumped out when the growth chamber is also pumped down to a predetermined vacuum.

In operation, the power source 50 delivers about 100 W of electrical power to the vitreous C filament 40.1, which resistively heats the filament 40.1 to a temperature in excess of 2000° C. (but below the vitreous-to-graphitic phase transition onset temperature of 2300° C.) in order to generate sufficient C vapor, for example, to dope a Group III-V compound layer or to grow a Si—C-based alloy layer.

EXAMPLE

The following design parameters illustrate the construction of a C effusion cell in accordance with an illustrative embodiment of our invention. Various materials, dimensions and operating conditions are provided by way of illustration only and, unless otherwise expressly stated, are not intended to limit the scope of the invention.

Filament 40.1: vitreous C with approximate dimensions $d_1$=12 mm; $d_2$=22 mm; $d_3$=28 mm; $w_1$=2 mm; $w_2$=6 mm, and t=0.5 mm Refractory rods 40.2: made of Ta; diameter=6 mm Holes 40.2b in rods 40.2: diameter=0.5 mm Conductive rods 60.1: made of Cu; diameter=6 mm Washers 40.6: made of 93% Ta, 7% W Bolts 40.7: made of Ta Spacers 40.5: made of Re foil Input power: ~100 W (~18.4 A at ~6 V), which produces a filament temperature of about 2100° C. (±100° C.)

We have successfully operated this type of vitreous C filament in an MBE apparatus to grow Group III-V epitaxial layers doped with C for over 100 hr without observing any significant degradation of the filament or its ability to deliver acceptable C flux.

More specifically, we have fabricated a high mobility, two-dimensional hole system (2DHS) confined in GaAs/AlGaAs quantum wells grown by MBE on the [100] surface of GaAs. The quantum wells were modulation doped with C utilizing our invention. At a temperature of 0.3° K. and carrier density of about p=$6\times10^{10}$ cm$^{-2}$, a mobility of about $3.0\times10^6$ cm$^{-2}$ Ns was achieved.

More generally, we have achieved C doping levels of $7\times10^{18}$ cm$^{-3}$ in bulk doped GaAs structures, but higher doping levels can be achieved in several ways. First, the temperature of the filament 40.1 may be increased while remaining below the aforementioned phase transition onset temperature. Second, the growth rate may be decreased. Third, the growth may be pulsed; i.e., one or more of the sources (e.g., a Ga source) may be turned on and off at prescribed times to effectively reduce the growth rate while the C source remains on to increase the C doping level.

It is to be understood that the above-described arrangements are merely illustrative of the many possible specific embodiments that can be devised to represent application of the principles of the invention. Numerous and varied other arrangements can be devised in accordance with these principles by those skilled in the art without departing from the spirit and scope of the invention. In particular, the C filament may be heated by well known techniques other than by passing an electric current through it. For example, the C filament may heated by electromagnetic energy; e.g., by an RF signal from a radio frequency source or by an optical signal from a high power laser, such as a $CO_2$ laser.

We claim:

1. An effusion source comprising
    a vitreous carbon filament, and
    a heater to increase the temperature of said filament to produce a carbon vapor,
    wherein said heater is configured to pass electric current through said filament so that said filament is resistively heated and carbon is evaporated therefrom and
    wherein said vitreous carbon filament comprises an elongated planar member having relatively wide end portions connected by a narrower central portion.

2. The effusion source of claim 1, further including a pair of spaced apart rods having coplanar ends, said member being supported across said ends.

3. The effusion source of claim 2, wherein said heater includes said rods configured to deliver electric current to said member to heat said member and produce said carbon vapor.

4. The effusion source of claim 3, wherein said rods comprise a refractory metal.

5. The effusion source of claim 4, further including a spacer disposed between each of said rods and said member, said spacer comprising a material selected from the group consisting of rhenium, tungsten and alloys of either of them.

6. The effusion source of claim 5, wherein each of said rods has a threaded bore extending along the longitudinal axis thereof, said spacers and said member have boles aligned with said bores, and further including a pair of bolts having threaded shafts that extend through said holes and into said bores, said bolts being configured to secure said member.

7. The effusion source of claim 6, wherein each of said bolts has a head attached to its shaft, and further including a resilient washer disposed between said head and said member.

8. The effusion source of claim 7, wherein said resilient washer comprises a Beilville washer.

9. The effusion source of claim 8, wherein said bolt and said washer comprise tantalum.

10. The effusion source of claim 6, wherein each of said rods has a hole extending transverse to the longitudinal axis thereof, said hole being in gas flow communication with said bore.

11. A method comprising:
    (a) depositing a layer of material on a substrate, and
    (b) during step (a), passing electric current through a body of material that includes vitreous carbon so that carbon from said body is vaporized and incorporated into said layer, wherein step (a) deposits a layer comprising a Group III-V compound material, and step (b) incorporates said carbon into said layer as a dopant.

12. The method of claim 11, wherein step (a) deposits said layer as a Group III-V compound semiconductor.

13. The method of claim 11, wherein step (a) deposits a layer comprising an alloy of Si and at least one other primary constituent, and step (b) incorporates said carbon into said layer as one of said primary constituents.

* * * * *